United States Patent

Pfirrmann

[11] 4,337,251
[45] Jun. 29, 1982

[54] METHOD OF AVOIDING AND REMOVING ADHESIONS

[75] Inventor: Rolf W. Pfirrmann, Lucerne, Switzerland

[73] Assignee: Ed. Geistlich Sohne AG fur Chemische Industrie, Lucerne, Switzerland

[21] Appl. No.: 147,231

[22] Filed: May 6, 1980

[30] Foreign Application Priority Data

May 9, 1979 [GB] United Kingdom ................. 7916017

[51] Int. Cl.³ ............................................. A61K 31/54
[52] U.S. Cl. .................................................... 424/246
[58] Field of Search ......................................... 424/246

[56] References Cited

FOREIGN PATENT DOCUMENTS 1124285 8/1968 United Kingdom ................ 424/246

OTHER PUBLICATIONS

CA 88:27803t (1978).
CA 86:115123k (1977).
CA 84:39312n (1976).

Primary Examiner—Frank Cacciapaglia, Jr.
Attorney, Agent, or Firm—Bacon & Thomas

[57] ABSTRACT

The invention provides a method of treatment of the human or animal body comprising the application of an aqueous solution containing a compound of formula I

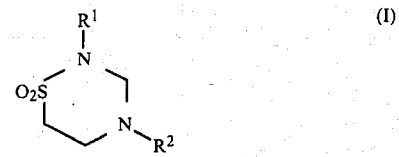

[wherein $R^1$ represents a hydrogen atom or an alkyl group having from 1 to 6 carbon atoms and $R^2$ represents a hydrogen atom, an alkyl group having from 1 to 6 carbon atoms or a group of formula II

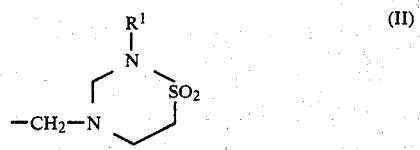

in which $R^1$ is as defined above] to human or animal tissue subjected to surgical treatment whereby the incidence of adhesion formation is eliminated or substantially reduced or whereby existing adhesions are at least substantially detached or unblocked. There is also provided a solution for use in the above method.

19 Claims, No Drawings

METHOD OF AVOIDING AND REMOVING ADHESIONS

This invention relates to a novel method of combatting the formation of adhesions resulting from surgery.

When tissues such as the intestines or the pericardial sac are subjected to surgical treatment, there is a tendency for adhesions to form which join the affected tissues to neighboring areas. In the case of the intestines, adhesions between sections of the bowel inhibit its natural movement in such a way that acute bends form and are held in position thereby causing a bowel obstruction. Indeed peritoneal adhesions have now replaced external hernia as the commonest cause of bowel obstruction. As the number of patients subjected to laparotomy increases, so does the incidence of obstruction due to adhesions. Similarly, after many other types of surgery, it is found, on further surgery at the same location, that extensive adhesion formation has taken place, greatly impeding the second surgical operation. Surgeons have been searching for a means of preventing adhesions for decades and many different materials have been tried.

We have now found that aqueous solutions of the compound Taurolin and its analogues as described in our British Pat. No. 1124285 are effective in preventing such adhesions if applied to the site of a surgical operation before, during and/or after surgery.

According to one aspect of the present invention there is provided a method of treatment of the human or animal body comprising the application of an aqueous solution containing a compound of formula I

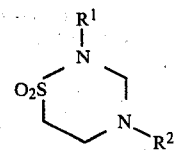

[wherein $R^1$ represents a hydrogen atom or an alkyl group having from 1 to 6 carbon atoms and $R^2$ represents a hydrogen atom, an alkyl group having from 1 to 6 carbon atoms or a group of formula II

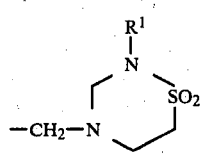

in which $R^1$ is as defined above] to human or animal tissue subjected to surgical treatment whereby the incidence of adhesion formation is eliminated or substantially reduced or whereby existing adhesions are at least substantially detached or unblocked. The above application conveniently is effected for at least part of the time from shortly before to shortly after the said surgical treatment.

According to a further aspect of the present invention there is also provided, for use in the method of the present invention described above, an aqueous solution containing a compound of formula I as defined above.

For the sake of convenience, these solutions are termed herein the "active solutions."

It is particularly preferred that Taurolin itself should be used, namely bis-(1,1-dioxo-perhydro-1,2,4-thiadiazin-4-yl)-methane ($R^1$=H, $R^2$=formula II).

We have found that using solutions of Taurolin in this way, adhesions may be prevented or, if they do form, be restricted to a flimsy and virtually insignificant form.

According to a yet further aspect of the present invention there is provided a pack comprising a solution as described above together with instructions for the use of the said solution in a method of treatment of the human or animal body by the application of the said solution to human or animal tissue subjected to surgical treatment, by which application the incidence of adhesion formation is eliminated or substantially reduced or whereby existing adhesions are at least substantially detached or unblocked. In the packs according to the present invention it is preferable that the compound of formula I present in the said solution should be Taurolin itself; the instructions conveniently indicating a daily dose of said solution of from 2 to 20 g of Taurolin.

The term "surgery" as used herein is intended to include not only operations involving cutting of tissues but also other operative manipulations such as diathermy or even simple handling of certain tissues.

As indicated above, a primary occurance of adhesions is in peritoneal surgery, when adhesions may form linking one or more sections of the bowel with other sections or the wall of the peritoneal cavity. In heart operations, adhesions from the pericardial sac to neighboring tissues may eventually inhibit the free movement of the heart and greatly impede second surgical operations. Adhesions are also a common cause of blockage of the fallopian tubes leading to sterility in women.

In all these cases, the active solution should be desirably applied to all the tissues exposed to treatment at least in the period just prior to the end of the operation. It may be convenient to apply the solution throughout. In many cases it may even be desirable to continue application by instillation, for example through a catheter into the peritoneum.

We have also found that the active solutions can in many cases unblock or detach adhesions which have already formed due to previous surgery.

The concentration of the substance of formula (I) is preferably in the range 0.5 to 5% by weight, depending, at the maximum, on the solubility of the compound. Solutions of 1.0 to 2.0% Taurolin are particularly preferred.

In order to achieve relatively high concentrations of Taurolin and relatively insoluble compounds of formula (I), it may be useful to incorporate polyvinylpyrrolidone (PVP) in the solution, e.g. at a concentration in the range 4 to 7% by weight. The molecular weight of the PVP should not be greater than 30,000 and is preferably less than 10,000, for example between 2000 and 3500. Kollidone 12 sold by BASF is especially suitable. Such PVP is relatively quickly resorbed and excreted renally.

A particular advantage of the compounds of formula (I) and more especially Taurolin, is their very low toxicity. They have previously been known purely as bacteriocides having an unusual secondary action against bacterial endotoxins and are effective in transferring methylol groups to the bacterial material or the toxins while liberating taurinamide or a simple derivative thereof. Taurine is found naturally in the body and is particularly non-toxic.

Due to the above effect against bacterial endotoxins, Taurolin has been used in peritoneal operations where bacterial infection is present, as in faecal peritonitis. It has not, however, been proposed for use in surgery where no bacterial infection is present and would not have been expected to be useful in such a context.

A further advantage of Taurolin is its stability in aqueous solution, enabling the solutions to be pre-packed and stored over relatively long periods. Furthermore, it has recently shown to be non-teratogenic in mice (unpublished).

The quantity of Taurolin applied according to the invention during surgery, will vary greatly with the operation. A liberal flow of the solution over the tissues concerned is necessary and in general between 2 and 20 g Taurolin will be administered per 24 hours for an adult human, e.g. by intraperitoneal infusion or instillation using a fine catheter into the abdomen.

The following Example of a solution for use in the method of the invention is given below:

EXAMPLE

| | |
|---|---|
| Bis-(1,1-dioxo-perhydro-1,2,4-thiadiazin-4-yl)-methane | 400 g |
| Polyvinylpyrrolidone (Kollidone 17) | 1000 g |
| Sterile water | to 20 liters |

15 liters double distilled pyrogen free water are filled into a 25 liter glass vessel with stirrer and intensive reflux device and heated to 50° C. with stirring. The Taurolin (400 g) is added followed by PVP (Kollidone 17; 1000 g). After dissolution, the solution is cooled and the pH adjusted to 6.0 with a few drops pf 0.1 N hydrochloric acid. The solution is then passed through an adsorption filter to remove microorganisms and pyrogens and through a sterilising millipore filter before being filled into 100 ml vials which are finally autoclaved.

What is claimed is:

1. A method of treatment of a human or animal in need of said treatment comprising the application of an aqueous solution containing a compound of formula I

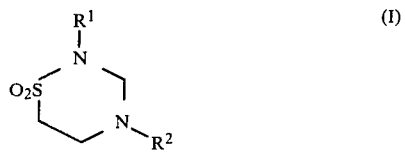

wherein $R^1$ represents a hydrogen atom and $R^2$ represents a hydrogen atom or a group of formula II

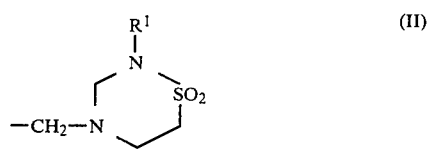

in which $R^1$ is as defined above to human or animal tissue subjected to surgical treatment where no bacterial infection is present whereby the incidence of adhesion formation is eliminated or substantially reduced or whereby existing adhesions are at least substantially detached or unblocked.

2. A method as claimed in claim 1 wherein the said application is effected for at least part of the time from shortly before to shortly after the said surgical treatment.

3. A method as claimed in claim 1 wherein the concentration of the said compound of formula I in the said aqueous solution is from 0.5 to 5% by weight.

4. A method as claimed in any one of claims 1 to 3 wherein the said compound of formula I is bis-(1,1-dioxo-perhydro-1,2,4-thiadiazin-4-yl)-methane.

5. A method as claimed in claim 4 wherein the dosage of bis-(1,1-dioxo-perhydro-1,2,4-thiadiazin-4-yl)-methane is from 2 to 20 g per day for an adult human.

6. A method as claimed in claim 1 wherein the said aqueous solution further contains polyvinylpyrrolidone.

7. A method as claimed in claim 6 wherein the molecular weight of the polyvinylpyrrolidone is less than 30,000.

8. A method as claimed in claim 6 wherein the molecular weight of the polyvinylpyrrolidone is less than 10,000.

9. A method as claimed in claim 6 wherein the molecular weight of the polyvinylpyrrolidone is from 2,000 to 3,500.

10. A method as claimed in claim 1 wherein the said solution is applied by instillation or by infusion.

11. A method as claimed in claim 1 wherein the said surgical treatment involves surgery of the peritoneum, the heart or the fallopian tube.

12. A method of treatment of a human or animal in need of said treatment comprising the application of an aqueous solution containing a compound of formula I

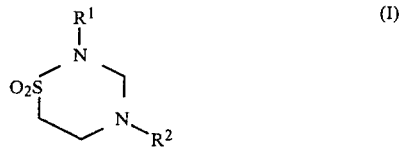

wherein $R^1$ represents a hydrogen atom and $R^2$ represents a hydrogen atom or a group of formula II

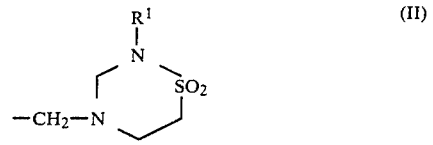

in which $R^1$ is as defined above to human or animal tissue subjected to surgical treatment whereby existing adhesions are at least substantially detached or unblocked.

13. A method as claimed in claim 12 wherein the said application is effected for at least part of the time from shortly before to shortly after the said surgical treatment.

14. A method as claimed in claim 12 wherein the concentration of the said compound of formula I in the said aqueous solution is from 0.5 to 5% by weight.

15. A method as claimed in any one of claims 12 to 14 wherein the said compound of formula I is bis-(1,1-dioxo-perhydro-1,2,4-thiadiazin-4-yl)-methane.

16. A method as claimed in claim 12 wherein the said solution is applied by instillation or by infusion.

17. A method as claimed in claim 12 wherein the said surgical treatment involves surgery of the peritoneum, the heart or the fallopian tubes.

18. A method as claimed in claim 12 wherein the said aqueous solution further contains polyvinylpyrrolidone.

19. A method as claimed in claim 18 wherein the molecular weight of the polyvinylpyrrolidone is less than 30,000.

* * * * *